US010451745B1

(12) United States Patent
Bonal et al.

(10) Patent No.: US 10,451,745 B1
(45) Date of Patent: Oct. 22, 2019

(54) MUON DETECTORS, SYSTEMS AND METHODS

(71) Applicants: National Technology & Engineering Solutions of Sandia, LLC, Albuquerque, NM (US); National Security Technologies LLC, Las Vegas, NV (US); Decision Sciences International Corporation, Poway, CA (US)

(72) Inventors: Nedra D. Bonal, Albuquerque, NM (US); Leiph A. Preston, Albuquerque, NM (US); David Schwellenbach, Los Alamos, NM (US); Wendi Dreesen, Los Alamos, NM (US); J. Andrew Green, North Las Vegas, NV (US); Michael Sossong, Ramona, CA (US)

(73) Assignees: National Technology & Engineering Solutions of Sandia, LLC, Albuquerque, NM (US); National Security Technologies LLC, Las Vegas, NV (US); Decision Sciences International Corporation, Poway, CA (US)

( * ) Notice: Subject to any disclaimer, the term of this patent is extended or adjusted under 35 U.S.C. 154(b) by 0 days.

(21) Appl. No.: 14/965,666

(22) Filed: Dec. 10, 2015

Related U.S. Application Data

(60) Provisional application No. 62/090,653, filed on Dec. 11, 2014, provisional application No. 62/090,679, filed on Dec. 11, 2014.

(51) Int. Cl.
*G01T 1/20* (2006.01)
*G01N 9/24* (2006.01)

(52) U.S. Cl.
CPC ............ *G01T 1/2018* (2013.01); *G01N 9/24* (2013.01)

(58) Field of Classification Search
None
See application file for complete search history.

(56) References Cited

U.S. PATENT DOCUMENTS

| | | | | |
|---|---|---|---|---|
| 7,470,905 | B1 * | 12/2008 | Goldberg | G01T 1/2935 250/251 |
| 8,275,567 | B2 * | 9/2012 | Lightfoot | G01T 1/167 250/252.1 |
| 2011/0035151 | A1 * | 2/2011 | Botto | G01V 5/04 702/2 |

OTHER PUBLICATIONS

Anghel, V. et al., "A plastic scintillator-based muon tomography system with an integrated muon spectrometer", Nuclear Instruments and Methods in Physics Research A 798 (2015), pp. 12-23.

Burns, J. et al., "Munn Scattering Tomography using Drift Chamber Detectors", Proceedings of Science, Technology and Instrumentation in Particle Physics 2014, Amsterdam, The Netherlands, 12 pages.

(Continued)

*Primary Examiner* — Edwin C Gunberg
(74) *Attorney, Agent, or Firm* — Daniel J. Jenkins

(57) ABSTRACT

A muon detector system capable of determining muon direction and flight trajectory or path is disclosed. The muon detector system includes scintillators for determining muon direction, and an array of muon detectors arranged in orthogonal layers for determining flight trajectory. The system can be used for tomographic and telescopic mode imaging, and may be used for imaging concealed and/or subterranean objects.

11 Claims, 5 Drawing Sheets

(56) References Cited

OTHER PUBLICATIONS

Jo, W.J. et al., "Design of a muon tomography system with a plastic scintillator and wavelength-shifting fiber arrays", Nuclear Instruments and Methods in Physics Research A 732( 2013), 568-572.

Jourde, K. et al., "Experimental detection of upward going cosmic particles and consequences for correction of density radiography of volcanoes", Geophysical Research Letters, vol. 40, (2013), pp. 6334-6339, doi:10.1002/2013GL058357.

Marteau, J. et al., "Implementation of sub-nanosecond time-to digital convertor in field-programmable gate array: applications to time-of-flight analysis in muon radiography", Meas. Sci. Technol. 25 (2014), 11 pages.

Pesente, S. et al., "First results on material identification and imaging with a large-volume muon tomography prototype", Nuclear Instruments and Methods in Physics Research A 604 (2009) pp. 738-746.

\* cited by examiner

MUON DETECTORS, SYSTEMS AND METHODS

CROSS-REFERENCE TO RELATED APPLICATIONS

This application claims priority to provisional patent applications U.S. Ser. No. 62/090,653, entitled "IMAGING METHODS USING UPWARD TRAVELING MUONS," by Bonal et al., filed Dec. 11, 2014, and U.S. Ser. No. 62/090,679, entitled "MUON DETECTOR," by Bonal et al., filed Dec. 11, 2014, the disclosures of which are incorporated herein by reference in their entirety.

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

TECHNICAL FIELD

Embodiments of the present invention relate to muon detectors, systems and methods more particularly relate to muon detectors having a muon path determination assembly located between scintillator panels that detect and measure muon path or trajectory and direction.

BACKGROUND

Technologies that detect concealed objects are important to the National Security mission. Muons are naturally occurring subatomic particles that can be utilized to image concealed objects similarly to x-ray imaging but unobstructed by materials like lead. Muons can penetrate the earth's crust up to several kilometers. High-energy cosmic ray muons are more sensitive to density variation than other phenomena, including gravity. Their absorption rate depends on the density of the materials through which they pass. Measurements of muon flux rate at differing trajectories provide density variations of the materials between the muon source (cosmic rays and neutrino interactions) and detector, much like a CAT scan. Currently, muon tomography can resolve features to the sub-meter scale.

Additionally, muons are highly penetrating, traveling distances of several kilometers through the earth. Muons were used to image the interior of the Pyramid of Khafre of Giza in the 1960's. More recently, muons have been used to image volcanoes and smaller objects like contents of cargo containers. Muon technology is being developed to image a variety of objects including drugs, tunnels, and nuclear waste.

Presently, imaging subsurface objects like tunnels using muons can be costly and access prohibitive as muon sensors must be placed below objects being imaged. In addition, current muon detectors are limited in that the direction the muon is traveling is usually assumed to be from above (the direction of the vast majority of flux), rather than measured.

What is needed are muon detectors, systems and muon detection methods that can overcome the limitation of the prior art.

SUMMARY OF THE DESCRIPTION

The present disclosure is directed to muon detectors, systems and methods for subsurface imaging using upward traveling muons.

The present disclosure is further directed to a novel muon detector capable of determining muon trajectory and direction.

In an embodiment, a muon detection system is disclosed that includes a muon detector, a processor; and a user interface. The muon detector includes a trajectory determination system and a scintillator assembly. The processor includes executable commands for determining the directionality of muons passing through the scintillator assembly and for determining a trajectory through which muons pass through the trajectory determination assembly.

In another embodiment, a muon detector is disclosed that includes a scintillator assembly and a trajectory determination system disposed between portions of the scintillator assembly.

In another embodiment, an imaging method is disclosed that includes arranging a muon detector capable of determining muon direction and trajectory with an object such that muons passing through or around the object are detected by the detector, and creating an image of the object from detected muons.

In another embodiment, an imaging method is disclosed that includes disposing an object between a first and a second muon detector, determining the direction and trajectory of muons passing through the first and second detectors, correlating the direction and trajectory of muons passing through the first and second detectors to determine the scattering angle of the muons, and creating an image of the object.

One advantage of the present disclosure is to provide a muon detector for subsurface imaging that accurately measures the direction the muon is traveling in addition to the trajectory or path the muon takes.

Another advantage of the present disclosure is to provide a muon detector for subsurface imaging that reduces costs and increases access to targets of interest.

Other features and advantages of the present disclosure will be apparent from the following more detailed description of the preferred embodiment, taken in conjunction with the accompanying drawings which illustrate, by way of example, the principles of the disclosure.

BRIEF DESCRIPTION OF THE DRAWINGS

Embodiments of the present invention are illustrated by way of example, and not limitation, in the figures of the accompanying drawings in which.

DETAILED DESCRIPTION

Described herein are muon detectors, systems and methods capable of accurately measuring the direction the muon is traveling and the trajectory or path the muon takes. In an embodiment, the detectors, systems and methods are used to accurately measure upward, downward, and horizontally traveling muons. The disclosed muon detectors may be used for imaging objects below and/or above ground. In an embodiment, the disclosed muon detectors can be used for subsurface imaging.

In the following description, numerous details are set forth. It will be apparent, however, to one skilled in the art, that the present invention may be practiced without these specific details. In some instances, well-known methods and devices are shown in block diagram form, rather than in detail, to avoid obscuring the present invention.

Reference throughout this specification to "an embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not mutually exclusive.

The terms "coupled" and "connected," along with their derivatives, may be used herein to describe structural relationships between components. It should be understood that these terms are not intended as synonyms for each other. Rather, in particular embodiments, "connected" may be used to indicate that two or more elements are in direct physical or electrical contact with each other. "Coupled" my be used to indicated that two or more elements are in either direct or indirect (with other intervening elements between them) physical or electrical contact with each other, and/or that the two or more elements co-operate or interact with each other (e.g., as in a cause and effect relationship).

Figure 1:
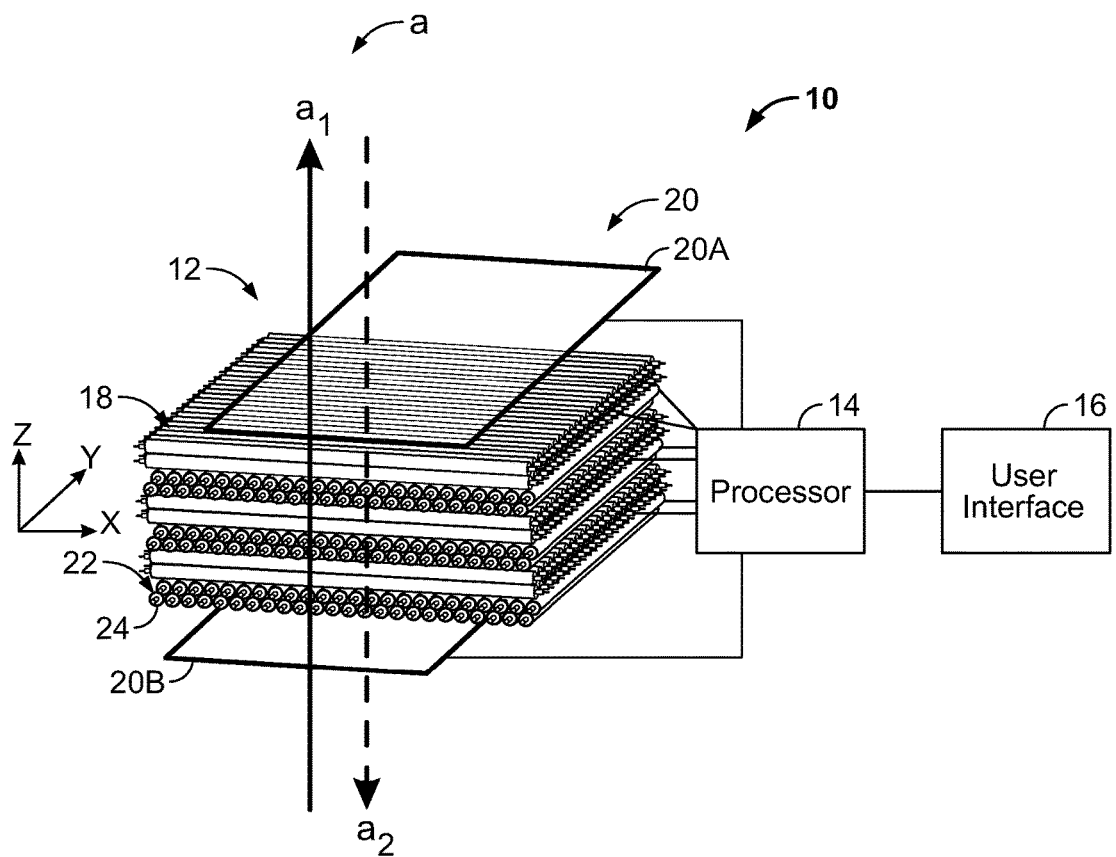
FIG. 1 is a schematic of a muon detector system according to an embodiment of the disclosure.

The term "upward traveling," "upward" or "upgoing" is defined as a muon traveling from below the horizontal (zenith angles between 90° and 180°) to earth center with an upward trajectory. For example, three sources of upgoing muons are: 1) back scattered, 2) neutrino interaction, and 3) "grazing" muons as shown in FIG. 1. Grazing muons refer to muons produced in the atmosphere that travel through a cord of the earth and travel upwards locally due to the earth's curvature.

The present disclosure is directed to a muon detector system capable of determining muon trajectory or path and direction. In this disclosure, the term "trajectory" and "path" are interchangeable and mean the curve along which the muon passed through the detector system without knowledge of which of the curve endpoints is the starting (entry) or ending (exit) point. Also in this disclosure, the term "direction" means the orientation from which the muon originates before detection the muon traveled along the path thus uniquely defining the starting and ending points of the path, or in other words, from which orientation a muon was first detected by a scintillator. FIG. 1 shows an embodiment of a muon detector system 10 according to the present disclosure. As can be seen in FIG. 1, the muon detector system 10 includes a muon detector (detector) 12, a processor 14 and a user interface 16. The muon detector 12 includes a trajectory determination assembly 18 and a scintillator assembly 20 for direction determination.

The trajectory determination assembly 18 is formed of layers of position sensitive detectors. In this exemplary embodiment, the trajectory determination assembly 18 is a drift tube assembly that includes six sheets or layers 22 of drift tubes 24 stacked in a Z direction. In another embodiment, the drift tube assembly may include four or more layers 22. In yet another embodiment, the drift tube assembly may include between four and ten layers. The number of layers 22 can be increased, however, as the number of layers 22 increases, the cost increases and portability of the detector 12 decreases. Additionally, as the number of layers 22 in the detector 12 is increased at a fixed size, the angular acceptance goes down, limiting the field of view. This is because each muon must pass through the topmost and bottommost layer 22 to be accepted.

Figure 1A:
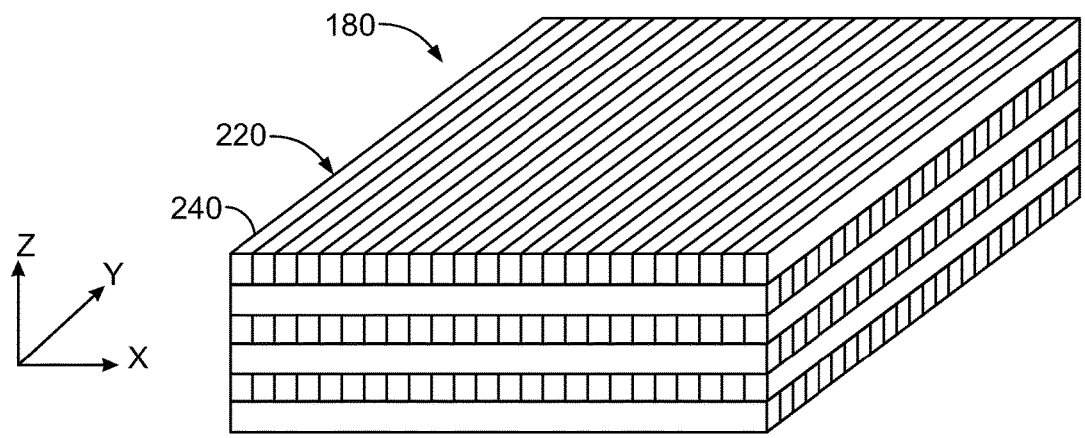
FIG. 1A shows an embodiment of a trajectory determination assembly according to an embodiment of the disclosure.

In another embodiment, the trajectory determination assembly 18 may be formed of other position sensitive detectors or arrangements. FIG. 1A shows an embodiment of another trajectory determination assembly 180. In this exemplary embodiment, the trajectory determination assembly 180 is formed of orthogonal layers 220 of position sensitive strips 240. The position sensitive strips 240 are charged particle or muon detectors that may be scintillator bars, silicon strips, resistive plate chambers, drift tubes, drift chambers, muon detector chambers, scintillator fibers, or other muon or charged particle activated materials or devices. In this exemplary embodiment, the position sensitive strips 240 have a circular cross-section, however, in other embodiments, the position sensitive strips 240 may have circular, square, rectangular, triangular or other geometries that allow for the layering of the strips in an area coverage pattern. In FIG. 1A, the trajectory determination assembly 180 is formed of six orthogonal layers of position sensitive strips. In another embodiment, the trajectory determination assembly 180 may be formed of two or more layers. In yet another embodiment, the trajectory determination assembly 180 may be formed of between four and ten layers.

Referring again to FIG. 1, each layer 22 includes a plurality of muon drift tubes (drift tubes) 24 arranged parallel to one another. In this exemplary embodiment, the drift tubes 24 are stacked in two layers in each layer 22. In another embodiment, a layer 22 may be formed of one, two, three or more layers of drift tubes. The layers 22 are stacked so that the drift tubes 24 of adjacent layers have their major tube axis perpendicular to those in the adjacent layer, or in other words, a plurality of orthogonal layers of drift tubes. Referring to FIG. 1, the drift tubes 24 are aligned in parallel and then stacked in X and Y directions. The intersection between the X and Y tubes hit by a muon helps constrain the location where the muon hit. Multiple X and Y layers of tubes provide greater resolution and the hit locations can be tracked through the layers 22 constraining the muon path.

Drift tubes 18 are known to those skilled in the art, and are generally formed of low conductivity metal tube casings having highly conductive metal filaments and an inert gas contained within, the functions of which are well known in the art. Each drift tube 24 provide an electrical impulse to the processor 14 via wires, power supplies, busses, and/or other electrical connections that provide electrical connectivity to the processor as would be understood by one of ordinary skill in the art. Note that in FIG. 1, the leads are shown each drift tube layer 22 instead of each drift tube 24 for clarity.

In this exemplary embodiment, the scintillator assembly 20, used to determine muon direction, includes two scintillator plates 20A, each located or positioned at opposite ends of the trajectory determination assembly 18. In other embodiments, the scintillator assembly 20 may include one or more scintillator plates located on opposite sides of the trajectory determination assembly 18. The scintillator plate's major plane is parallel to the major plane of the drift tube layers 22. Scintillator plates 20A for detecting muons are known in the art, and in this exemplary embodiment, are formed of a plastic material forming scintillator plates having long attenuation length, high light output and fast timing. In other embodiments, the scintillators may be formed of crystal or liquid scintillator materials. A photon is emitted when a muon or other ionizing particle hits the scintillator plates 20A. The photon is detected by a photon detector, such as, but not limited to a photomultiplier tube, a photodiode or silicon photomultiplier (SiPM), which multiplies the current generated by the photon. This detection method allows sub-nanosecond detection of particles, where the time difference between scintillators 20A and 20B is used to determine muon "a" direction. The muon $a_1$ indicated by the solid arrow would show a hit time in 20B prior to that of 20A. The muon $a_2$ indicated by the dashed arrow would show a hit time in 20A prior to that of 20B.

When muons and other charged particles hit and/or travel through scintillating materials, photons are emitted through ionization. A photomultiplier tube (not shown) is used to amplify the current to a measurable signal. In this exemplary embodiment, the photomultiplier tubes are shown as part of the processor 14, in other embodiments, the photomultiplier tubes may be a separate device or portion of a separate device from the processor 14. The photomultiplier tubes provide electrical impulses to the processor 14 via wires, power supplies, busses, and/or other electrical connections that provide electrical connectivity to the processor as would be understood by one of ordinary skill in the art. In this exemplary embodiment, each scintillator plate 20A is a single scintillator. In another embodiment, each scintillator plate 20A may be formed of one or more scintillators.

The processor 14 may include one or more filters, photon detectors such as photomultiplier tubes, photodiodes or silicon photomultipliers (SiPMs), amplifiers, computer processors, digital acquisition systems and executable programs for analyzing muon detection timing, direction, trajectory angle, intensity, and perhaps momentum. The processor 14 receives electrical impulses from the scintillator assembly 20 and tracks the time, location, and other necessary information from each photon event from each scintillator. Only muon events that are coincident within a predetermined time window on both scintillators are processed to determine which scintillator the muon hit first, which determines the direction the muon was traveling. The processor 14 also receives electrical impulses from the drift tube assembly 18 and tracks the time, location, and other necessary information from each event for each drift tube. Only muon events that are coincident on multiple drift tubes within a predetermined time window are processed to determine the trajectory angle the muon was traveling. The processor 14 provides the analysis results to the user interface 16.

The user interface 16 may be a monitor, stand-alone computer, computer terminal, laptop computer, computer tablet or other device that may include displays, input devices such as keyboard, mouse and touchpad, memory, computer processor unit (CPU) that allows a user to interface with the processor 14. In another embodiment, the processor 14 and computer interface 16 may be fully or partially combined.

In operation, muons pass through the detector 12 from either the A or B direction, as indicated by the arrows. As muons pass through a first and then a second scintillator (20A and 20B, respectively) on opposite sides of the drift tube assembly, photons are generated and collected at each scintillator 20A and provided to the processor 14 where one or more photomultiplier tubes generate an electrical signal that is analyzed by the processor 14. The processor 14 determines which electrical signal from each scintillator (20A or 20B) is the earliest and therefore determines from which primary direction (A or B) the muon originated.

Determining the direction a muon is traveling is important for some applications. Detectors record muons coming from the direction of the object of interest and from the opposite direction. This is usually not a problem when imaging objects using vertically traveling muons because muons traveling upward are insignificant compared to the large flux of downward traveling muons. Muon flux decreases with zenith angle by approximately $\cos^2$. This means that the greatest flux is from muons traveling vertically downward from a zenith angle of 0° and flux is significantly lower from muons traveling horizontally from a zenith angle of 90°. Imaging targets like mountains requires use of muons traveling nearly horizontally at high zenith angles. For this case, the flux of muons from the desired direction is on the order of the flux from the opposite direction, resulting in a significant amount of "noise." Determining the directionality each muon is traveling eliminates this source of noise.

The addition of muon directionality to detector systems will also widen the application space of muon technology. For example, the very low flux of muons traveling from below the horizon, which have an upward direction locally relative to the detector, can be exploited. Though acquisition times will be much longer than utilizing the more prevalent downward traveling muons, muon detectors on the ground surface can be used to detect targets underground.

The muons passing through the detector 12 also pass through the drift tube assembly 18. When muons and other charged particles pass through a volume of gas such as in gas wire detectors, otherwise referred to as drift tubes, electrons are knocked off and/or stripped from the gas atoms. These free electrons then drift toward a positively charged wire in the tube where gas amplification occurs creating a detectable signal. The distance away from the wire that the muon hit the gas and freed the electrons can be determined by the time taken for the electrons to drift through the gas to the wire. However, a single drift tube alone cannot determine the location along the drift tube where the muon hit. As the muons pass through drift tube layers 22, drift tubes 22 in those layers are excited. The electrical pulses for each drift tube 22 are sent to the processor 14 that determines the angle at which the muons passed through the detector 12. Note that in FIG. 1, the drift tubes 22 are shown connected to the processor 14 by a single line to the processor for simplicity. The processor 14 does this by fitting a line through the drift tubes that have been excited by the passing muons. In an embodiment, the system may include two or more detectors for increasing resolution.

Figure 2:
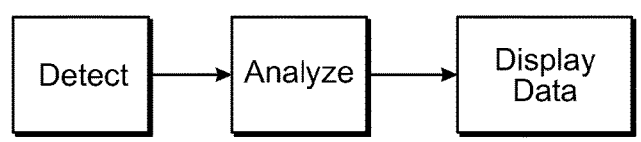
FIG. 2 is a flow chart of a method for imaging objects according to an embodiment of the disclosure.
Figure 2A:
FIG. 2A is a flow chart showing additional detail of the analyzing step of FIG. 2 according to an embodiment of the disclosure

The present disclosure is further directed to methods for using the disclosed muon detector system to image objects above or below ground. The objects may be in plain view or concealed. FIG. 2 is a flow chart of an embodiment of a method for imaging objects above or below ground using the disclosed muon detector system according to the present disclosure. FIG. 2A is a flow chart showing additional details of the processing step according to an embodiment of the disclosure. In FIG. 2A, the detector may be the path determination assembly and/or the scintillator assembly. As can be seen in FIGS. 2 and 2A, the method includes detecting muons, analyzing muons for path and direction, and outputting results to a user. The muons are detected for path by the path determination assembly and for direction by the scintillator assembly. The detections from those assemblies are then analyzed by the processor for path and direction.

Data from the drift tube assembly is processed by a digital acquisition system (DAS) included in the processor to record the time and location when an ionizing particle hits the detector. The data is then filtered to remove hits that are not from muons. For example, hits on only one drift tube most likely are from gammas and are removed. Also, detector hits that arrive earlier than expected are likely from delta rays or scattered electrons and are removed. Additionally, cosmic ray showers can produce multiple muon hits in a short time frame, making tracking of a single muon difficult. Data hits that are likely not muons, such as from cosmic ray showers or that cannot be tracked accurately, are filtered out.

The candidate muon hits are then tracked through the detector (e.g. through the different x and y layers of drift tubes) using an optimization algorithm. Tracks that do not meet a goodness of fit criteria between the observed and expected values are eliminated. Reconstruction algorithms then use the good tracks to create an image. Common reconstructions rely on voxels for 3D images and pixels for 2D images. A hit on the voxel or pixel is defined if a muon is tracked through it. The hits are tabulated for each voxel or pixel and scattering angles are tabulated between voxel hits. Image resolution is related to the voxel or pixel size, the tracking resolution, and the number of muons entering each voxel. Longer acquisition times allow more muons to hit the detector and resolution is increased.

In determining muon direction, the processor determines which scintillator panel was hit by a muon first based on timing and uses an algorithm to fit a straight line between the muon hit locations on drift tubes and scintillator panels. This provides the direction (e.g. right, left, up, down) the muon is traveling (based on which scintillator was hit first and which one was hit second) as well as the angle in three-dimensional space the muon was traveling.

Displaying data may include displaying images of muon counts at a particular point and/or coordinate travel paths and directions of detected muons for further use/processing by a user(s).

Other embodiments of methods for using the disclosed muon detector system to image objects above or below ground are further discussed in reference to examples provided below.

Tomographic Mode

Figure 3:
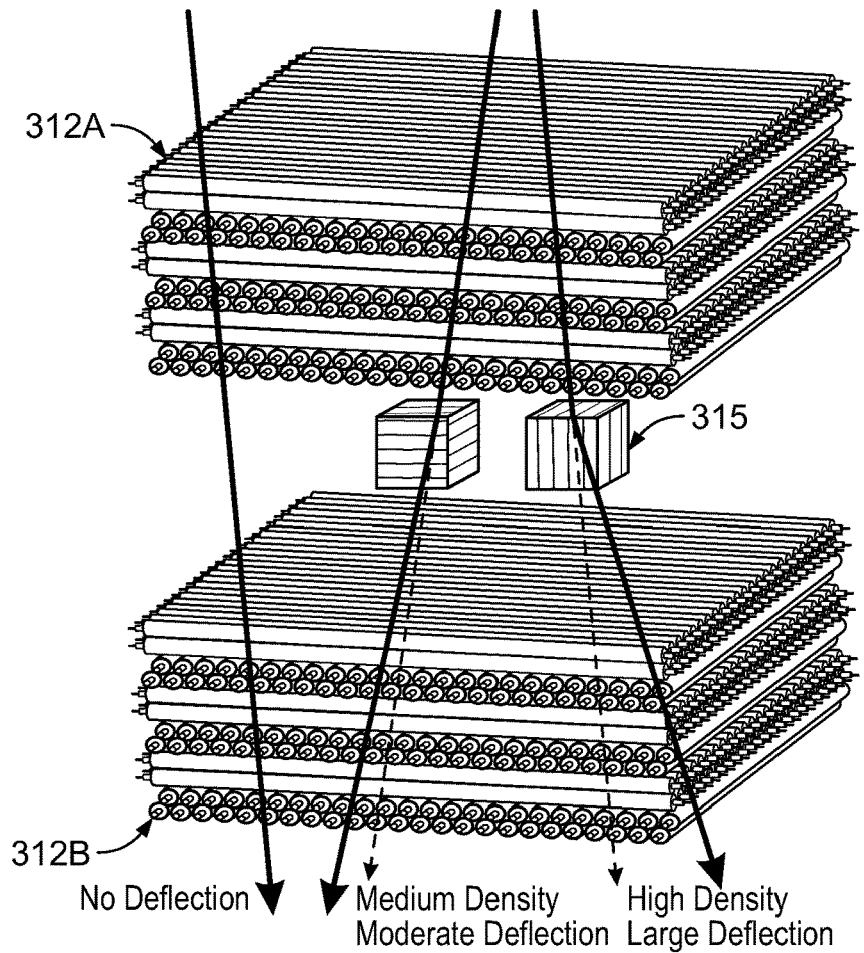
FIG. 3 shows a muon detector arrangement for objects to be imaged in tomographic mode according to an embodiment of the disclosure.

FIG. 3 illustrates a tomographic mode system arrangement according to an embodiment of the disclosure. The tomographic mode system uses two muon detectors 312A, 312B to image objects 315 located between the two detectors 312A, 312B. Two detectors 312A, 312B enable tracking of individual muons in and out of the volume between them. The tomographic mode of imaging with muons relies on Coulomb scattering of the muons. The scattering angle of the muon is governed by Z (atomic number) and density of the material the muon passed through within the imaging volume. This angle can be calculated between the two detectors for each muon and the material between the detectors can then be determined. Additionally, the location and size of the material can be mapped in three-dimensions. A drawback to the tomographic mode is that access to two sides of the object is required, which may not be practical for some objects and ideally the objects need to be small enough to fit between the two detectors.

As can be seen in FIG. 3, tomographic mode requires two detectors 312A and 312B, one on each side of one or more objects 315, so access to two sides of the object(s) is needed.

Tomographic Mode Example

Figure 4:
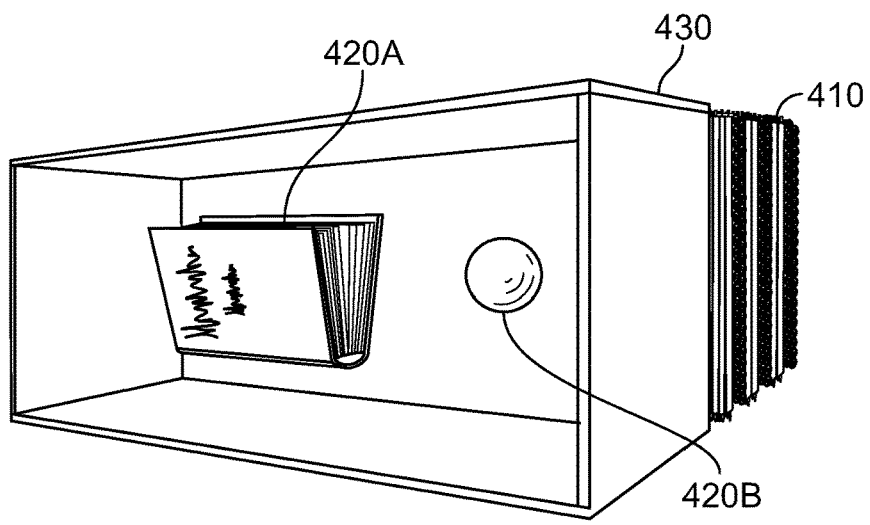
FIG. 4 is an illustration of an open lead box containing of a book (low-Z) and a sphere of tungsten (high-Z) inside a lead box.

FIG. 4 illustrates a tomographic mode system arrangement according to an embodiment of the disclosure. In this exemplary embodiment, the objects 420A, 420B are in a box 430. Box 430 is shown with a cover removed so as to expose the objects 420A, 420B for illustration purposes only. In this exemplary embodiment, a detector 410 is shown on the backside of the box 430. Another detector (not shown), is then placed on the front side of the box once the cover is put in place. In this embodiment, the detectors are arranged horizontally, however, in other embodiments, the detectors may be arranged in any orientation, including horizontally as shown in FIG. 3. In this exemplary embodiment, the detector 410 is shown proximate or in contact to the box 430, however, in other embodiments, one or both of the detectors may be positioned in contact with, proximate to, or at a distance from the box. Also in this embodiment, the objects are within a box, however, in other embodiments, one or more objects may be within a box or other structure. In another embodiment, one or more objects may be not within a box or other structure, as shown in FIG. 3.

Low and High Density Material Imaging in Tomographic Mode

Figure 5:
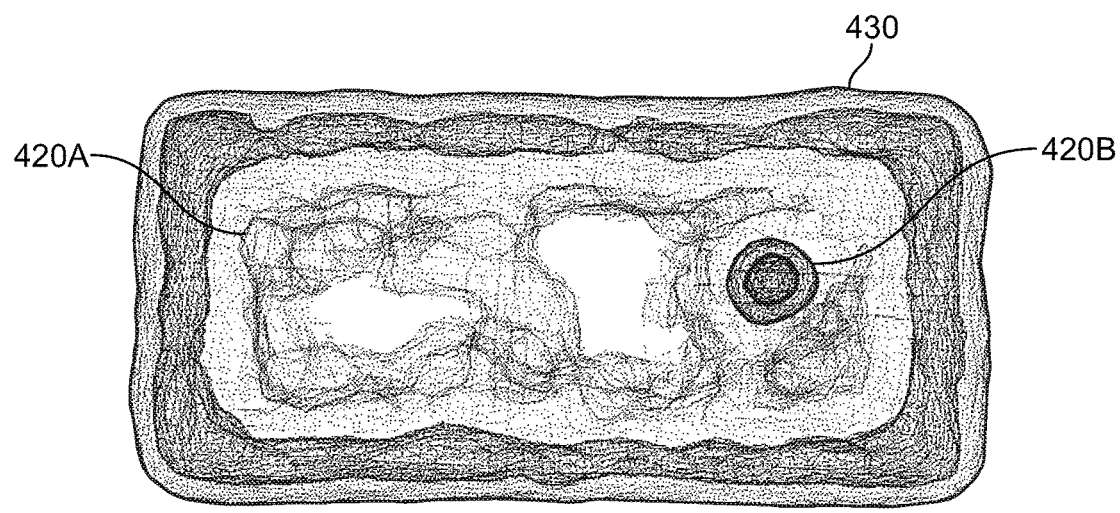
FIG. 5 is a muon image of the lead box containing the book and sphere of tungsten of FIG. 4.

Muons are sensitive to densities. Therefore, muon data can be used to determine relative density differences of objects. Tomography may be used for locating concealed high-Z (atomic number) material like plutonium and low-Z material like drugs. FIG. 5 illustrates the results of an experiment to assess muon tomography for detection of low-Z material. Referring to FIG. 4, a book (low-Z) 420A and a sphere of tungsten (high-Z) 420B were placed inside a lead box 430 as shown in FIG. 4 (note that one side of box is open and the second detector is not shown for illustration purposes). Muon data were collected over 1440 minutes (24 hours) using tomographic mode.

FIG. 5 shows a horizontal slice of a 3D image of the lead box 430 and contents 420A, 420B constructed from the muon hits and scattering angles. Darker shades in the reconstructed image represent the higher Z material tungsten sphere 420B. The outline of the low-Z book 420A is also distinguished in the image. This experiment demonstrates the capability of muon tomography for detection of concealed materials.

Telescopic Mode

Figure 6:
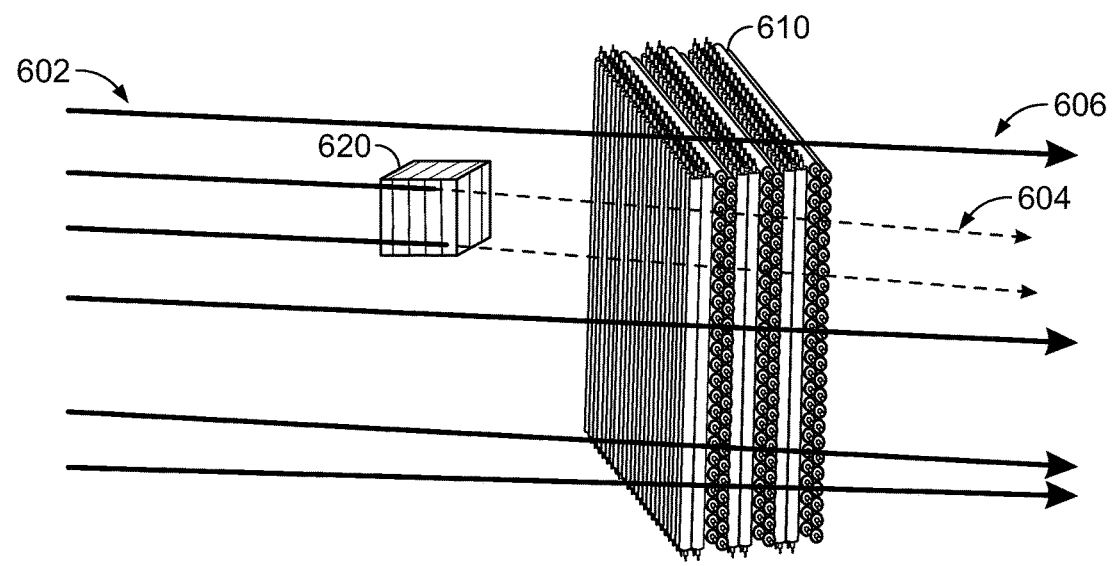
FIG. 6 shows a muon detector arrangement for objects to be imaged in telescopic mode according to an embodiment of the disclosure.

Telescopic mode may be referred to as transmission muon radiography and can produce 2D images of objects, similar to x-ray and gamma ray radiography. Also, very large objects like volcanoes can be imaged using this mode. As can be seen in FIG. 6, telescopic mode requires only one detector 610 on one side of an object 620, so access to only one side of the object is needed. However, lower resolution images are produced because the scattering angle of the muon through material cannot be measured. Additionally, acquisition times are typically longer since less information (no scattering angles) is obtained. Telescopic mode relies on attenuation of the number of muon (flux) passing through the materials because the incoming cosmic ray muon flux is fairly constant. More muons are attenuated in higher density materials so the flux is lower compared to lower density materials like air for example. Telescopic mode is often used to detect muons that are traveling nearly horizontally, like those needed to image a mountain. In another embodiment, two or more detectors may be used on one side of the object to improve resolution or construct 3D images of the scene. As can be seen in FIG. 6, muons 604 passing through the object 620 are attenuated, and muons 606 not passing through the object 620 are not attenuated in the same manner. From this attenuation, an image of object 620 can be created from the detected muons 604, 606. In another embodiment, an object(s) may or may not be concealed and the detector may be placed above, below or alongside of one or more objects to be imaged. In another embodiment, the objects may be above ground and the detector may be placed below ground.

Deeply Concealed Object Detection in Telescopic Mode

Figure 7:
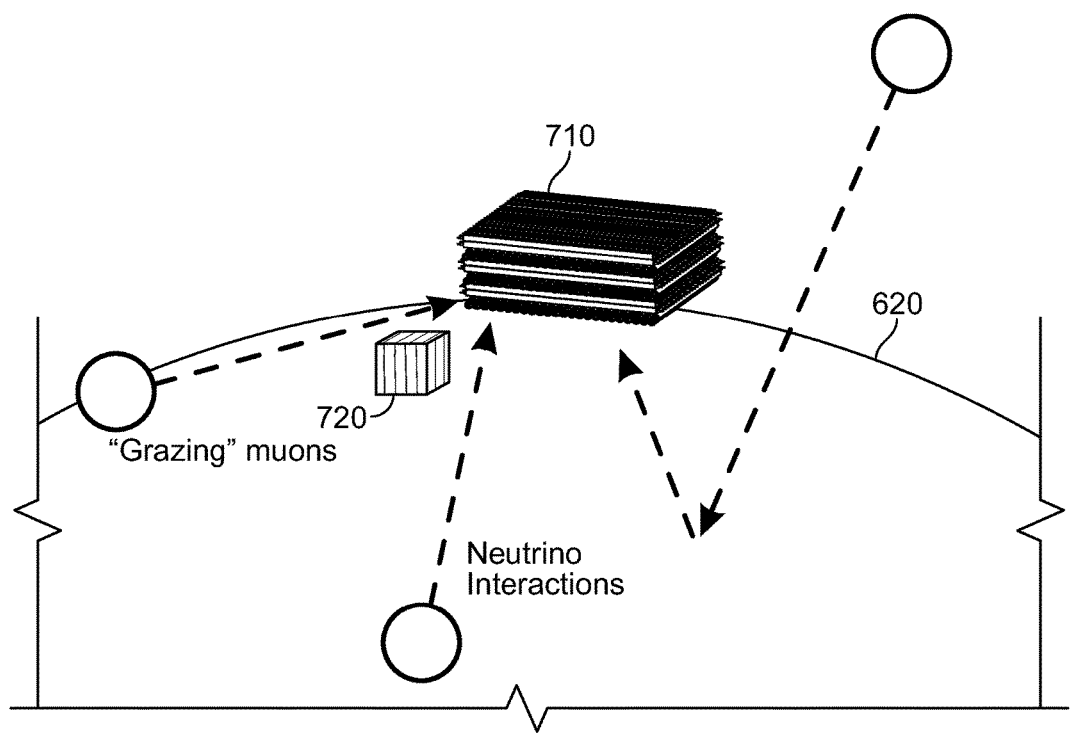
FIG. 7 shows an embodiment of an arrangement of a muon detector in telescopic mode for detecting objects below ground according to an embodiment of the disclosure.

FIG. 7 shows an embodiment of an arrangement of a muon detector 710 in telescopic mode for detecting an object 720 below ground 730 according to an embodiment of the disclosure. As can be seen in FIG. 7, the muon detector 710 has been placed above ground 730. A muon detector processor (not shown) has been configured to only detect and track muons impinging the detector 710 from below the ground surface (in this case, impinging upon the bottom side of the detector facing the earth). In such a manner, objects such as caves, rooms or vaults, generically shown by box 720 can be imaged by upward traveling muons that both pass through the object 720 and are attenuated by the object and by those that do not pass through the object. All muons (e.g. grazing, back scattered, neutrino interactions) can be detected. Grazing and back scattered muons are produced from cosmic ray interactions within the earth's atmosphere where neutrino interactions within the earth are part of the natural background radiation. Some neutrinos within the earth are transformed and arrive at the detector as muons. In another embodiment two or more muon detectors may be used. In another embodiment, one or more muon detectors may be placed below ground in a tunnel, vault, or borehole.

Applications Technology

Muon technology can be useful for various applications. Scattering from high-Z (atomic number) materials makes muons effective for locating special nuclear materials like plutonium and uranium. Muons are highly penetrating making them effective at detecting targets that are concealed in lead, which x-rays cannot penetrate. Additionally, muons can be used to image inside buildings without being inside the building by using horizontally traveling muons. Muon technology can be used to track and monitor nuclear waste containers in repositories. Underground caverns such as those used for the US Strategic Petroleum Reserves can be assessed using muons by mapping density contrasts. Similarly, tunnels and underground facilities can be detected using muons.

Locating and characterizing underground engineered structures such as tunnels and caverns are important to areas of energy surety, nonproliferation, and border and facility security. Examples include: cavern volume assessment, discovery of "hidden" rooms during treaty verification inspection, and monitoring high-value sites for subsurface intrusion. Voids created by these structures have a marked density contrast with surrounding materials, so using methods sensitive to density variations would be ideal. Muons are subatomic particles that are more sensitive to density variation than other phenomena and can penetrate the earth's crust several kilometers. Their absorption rate depends on the density of the materials through which they pass.

It is to be understood that the above description is illustrative, and not restrictive. For example, while flow diagrams in the figures show a particular order of operations performed by certain embodiments of the invention, it should be understood that such order is not required (e.g., alternative embodiments may perform the operations in a different order, combine certain operations, overlap certain operations, etc.). Furthermore, many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. The scope of the invention should, therefore, be determined with reference to the appended claims, along with the full scope of equivalents to which such claims are entitled.

What is claimed is:

1. A muon detection system, comprising:
   a muon detector, comprising:
      a trajectory determination system; and
      a scintillator assembly;
   a processor; and
   a user interface
   wherein the processor comprises executable commands for determining the directionality of muons passing through the scintillator assembly and for determining a trajectory through which muons pass through the trajectory determination assembly;
   wherein the processor further comprises executable commands for imaging an object not located within the muon detector; and
   wherein the processor includes instructions that when executed processes muon detections in telescopic mode by processing detections by the muon detector to determine attenuation of muons to produce a 2-dimensional image of an object.

2. The muon detection system of claim 1, wherein the trajectory determination system comprises two or more layers of muon drift tubes arranged orthogonally.

3. The muon detection system of claim 1, wherein the scintillator assembly comprises parallel scintillator plates disposed on opposite sides of the trajectory determination system.

4. The muon detection system of claim 2, wherein the two or more layers is between 4 and 10 layers.

5. The muon detection system of claim 1, wherein the trajectory determination system comprises two or more layers of charged particle detectors comprising a plurality of position sensitive strips selected from a group consisting of scintillator bars, silicon strips, resistive plate chambers, drift tubes, drift chambers, muon detector chambers, and scintillator fibers.

6. A muon detector, comprising:
   a scintillator assembly; and
   a trajectory determination system disposed between portions of the scintillator assembly; and
   a processor comprising executable commands for determining the directionality of muons passing through the scintillator assembly and for determining a trajectory through which muons pass through the trajectory determination assembly;

wherein the processor further comprises executable commands for imaging an object not located within the muon detector; and wherein the processor includes instructions that when executed processes muon detections in telescopic mode by processing detections by the muon detector to determine attenuation of muons to produce a 2-dimensional image of an object.

7. The muon detector of claim 6, wherein the trajectory determination system comprises two or more layers of muon drift tubes arranged orthogonally.

8. The muon detector of claim 6, wherein the scintillator assembly comprises parallel scintillator plates disposed on opposite sides of the trajectory determination system.

9. The muon detector of claim 7, wherein the two or more layers is between 4 and 10 layers.

10. The muon detector of claim 6, wherein each layer of the two or more layers of muon drift tubes comprises two layers of muon drift tubes.

11. The muon detector of claim 6, wherein the trajectory determination system comprises two or more layers of charged particle detectors comprising a plurality of position sensitive strips selected from a group consisting of scintillator bars, silicon strips, resistive plate chambers, drift tubes, drift chambers, muon detector chambers, and scintillator fibers.

* * * * *